United States Patent
Wang (10) Patent No.: US 10,235,752 B2
(45) Date of Patent: Mar. 19, 2019

(54) SLICE SELECTION FOR INTERPOLATION-BASED 3D MANUAL SEGMENTATION

(71) Applicant: INTERNATIONAL BUSINESS MACHINES CORPORATION, Armonk, NY (US)

(72) Inventor: Hongzhi Wang, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/357,667

(22) Filed: Nov. 21, 2016

(65) Prior Publication Data

US 2018/0144463 A1 May 24, 2018

(51) Int. Cl.
*G06T 7/00* (2017.01)
*A61B 6/00* (2006.01)
*A61B 6/03* (2006.01)

(52) U.S. Cl.
CPC ............ *G06T 7/0012* (2013.01); *A61B 6/032* (2013.01); *A61B 6/466* (2013.01); *A61B 6/503* (2013.01); *A61B 6/5211* (2013.01); *A61B 6/563* (2013.01); *G06T 7/0028* (2013.01); *A61B 2576/00* (2013.01); *G06T 2219/004* (2013.01)

(58) Field of Classification Search
CPC ....... G06T 3/0068; G06T 7/0012; G06T 7/30; G06T 7/33; G06T 2219/004; G06K 9/6218; A61B 6/5211; A61B 6/5217; A61B 6/5223
See application file for complete search history.

(56) References Cited

U.S. PATENT DOCUMENTS

| | | | |
|---|---|---|---|
| 5,633,951 A * | 5/1997 | Moshfeghi | 382/154 |
| 6,898,303 B2 | 5/2005 | Armato, III et al. | 382/131 |
| 8,612,890 B2 | 12/2013 | Nijlunsing et al. | 715/811 |
| 8,698,795 B2 | 4/2014 | Grewer et al. | 345/419 |
| 9,251,596 B2 | 2/2016 | Rueckert et al. | G06T 7/0089 |
| 2015/0205917 A1 | 7/2015 | Mabotuwana et al. | G06F 19/321 |
| 2016/0310761 A1* | 10/2016 | Li et al. | A61N 5/1039 |

* cited by examiner

*Primary Examiner* — Andrew W Johns
(74) *Attorney, Agent, or Firm* — Erik Huestis; Stephen Kenny; Foley Hoag LLP (57) ABSTRACT

Slice selection for interpolation-based 3D manual segmentation is provided such that propagation error is minimized during 3D reconstruction. In various embodiments, a plurality of 2D images is read. Each of the plurality of 2D images represents a slice of a 3D volume. Deformable registration is performed between each adjacent pair of the plurality of 2D images. From the deformable registration, propagation error is estimated between each pair of the plurality of 2D images. The plurality of 2D images is clustered into a predetermined number of clusters. A slice is selected for annotation from each of the predetermined number of clusters.

20 Claims, 8 Drawing Sheets

SLICE SELECTION FOR INTERPOLATION-BASED 3D MANUAL SEGMENTATION

BACKGROUND

Embodiments of the present disclosure relate to slice selection for interpolation-based 3D manual segmentation, and more specifically, to selecting a predetermined number of slices such that propagation error is minimized during 3D reconstruction.

BRIEF SUMMARY

According to embodiments of the present disclosure, methods of and computer program products for slice selection for interpolation-based 3D manual segmentation are provided. A plurality of 2D images is read. Each of the plurality of 2D images represents a slice of a 3D volume. Deformable registration is performed between each adjacent pair of the plurality of 2D images. From the deformable registration, propagation error is estimated between each pair of the plurality of 2D images. The plurality of 2D images is clustered into a predetermined number of clusters. A slice is selected for annotation from each of the predetermined number of clusters.

DETAILED DESCRIPTION

Accurate ground truth generation for 3D datasets is essential in many anatomy recognition and disease understanding applications. Interpolation techniques of the present disclosure can substantially reduce the cost of manual segmentation for 3D images by only requiring a subset of 2D slices to be manually segmented, from which 3D segmentation is reconstructed through inter-slice label propagation. According to various embodiments of the present disclosure, adaptive slice selection is applied to further speed up interpolation-based annotation.

Adaptive slice selection according to embodiments of the present disclosure reduces the overall label propagation errors from labeled slices to unlabeled slices. Given estimated pairwise label propagation errors between each slice pair, these methods select slices optimal for 3D segmentation reconstruction through clustering.

The methods herein are validated in a 3D cardiac CT anatomy annotation task. In the experiments, the slice selection methods described herein are compared with uniform selection. Adaptive slice selection methods further reduce about 10% of slices for manual annotation than uniform selection.

Given a 3D image with n 2D slices, for fast manual annotation, only a subset of the 2D slices are selected for manual segmentation. The 3D segmentation for the entire volume may be reconstructed by various methods such as interpolation or propagating and fusing labels from manually labeled slices to the remaining unlabeled 2D slices. However, anatomical information are not uniformly distributed in the space, and so uniform slice selection may not be optimal for 3D reconstruction. Accordingly, the present disclosure enables reduction in the number of slices for manual segmentation while preserving accuracy in the reconstructed 3D segmentation. In other words, when a fixed number of slices is selected for manual segmentation, the present disclosure minimizes errors in the reconstructed 3D segmentation.

3D segmentation reconstruction accuracy of interpolation methods depends on the overall label propagation accuracy. Accordingly, the slice selection problem is addressed herein by minimizing the overall label propagation errors from selected slices. Inter-slice propagation error is defined according to Equation 1, where $L_i$ is the manual segmentation of slice i and $L_{j \to i}$ is the warped manual segmentation from j to i. x indexes through a 2D slice. $I(\cdot)$ is an indication function.

$$E_{j \to i} = \sum_x I(L_{j \to i}(x) \neq L_i(x)) \qquad \text{Equation 1}$$

Let $S = \{s_1, \ldots, s_K\}$ be a set of K selected slices with $s_1 < \ldots < s_K$ and $\overline{S}$ be the set of unselected slices. The overall propagation error using S is given by Equation 2 where $c(S, i) = \text{argmin}_{j \in S} E_{j \to i}$ is the selected slice that produces the least propagation error for slice i. As discussed above, either $c(S, i) = \text{argmax}_{j < i, j \in S}$ or $c(S, i) = \text{argmin}_{j > i, j \in S}$. The selected slices should minimize the overall propagated error, i.e., $S = \text{argmin}_{|S|=K} E(S)$.

$$E(S) = \sum_{i \in \overline{S}} E_{c(S,i) \to i} \qquad \text{Equation 2}$$

With the above formulation, slice selection can be solved through clustering, where selected slices are cluster centers and the members of each cluster are slices that the cluster center produces the least propagation error for. Let matrix M stores pairwise propagation error between every slice pair, where $M(j, i) = E_{j \to i}$. Given M, slice selection is solved as set forth below. The clustering algorithm will converge to a local optimal solution from the initialization. To find a more global optimal solution, the clustering algorithm may be repeated multiple times with independently generated random initializations to return the solution giving the minimal overall propagation error. In the below experiments, the number of re-initializations is fixed at 1000.

According to various embodiments, a clustering algorithm for slice selection is provided as follows. For input $M_{n \times n}$ and K<n, cluster centers S are randomly initialized. Clusters are assigned for each slice as follows, for i=1 ... n, $c(S, i) = \text{argmin}_{j \in S} E_{j \to i}$. For each cluster, the members are calculated and the cluster center is updated as follows, for k=1 ... K, $C_k = \{j | c(S, j) = s_k\}$ and then $s_k = \text{argmin}_{i \in C_k} \Sigma_{j \in C_k} M(i, j)$. If no changes result from the above, or the maximal number of iterations is reached, S is returned. Otherwise, the process is repeated from cluster assignment.

Inter-slice label propagation error is estimated from image intensity differences according to Equation 3, where $F_i$ is the image for slice i and $F_{j \to i}$ is the warped image from slice j to slice i. α is a model parameter. The model captures the relations between segmentation label and image intensity, which is application dependent. The model parameter is mainly determined by three factors: 1) inter-slice registration accuracy, 2) noise levels in image acquisition and 3) how distinguishable different anatomical structures are based on intensity information. When inter-slice registration is accurate, noise level is low and anatomical structures can be well distinguished by intensity information, large a tends to fit the model better. Otherwise, small a may be more suitable.

$$p(L_{j \to i}(x) \neq L_i(x)) \propto |F_{j \to i}(x) - F_i(x)|^\alpha \qquad \text{Equation 3}$$

Using the intensity-based label propagation error model, M(j, i) is given by Equation 4.

$$M(j, i) = \begin{cases} \sum_{x \in ROI} |F_{j \to i}(x) - F_i(x)|^\alpha & |i - j| \leq D \\ \infty & |i - j| > D \end{cases} \qquad \text{Equation 4}$$

In general, registration is capable of reducing anatomical variations between nearby slices. For slices that are too far away, the anatomy content may be too different to be compensated by registration. Hence, label propagation is only considered between nearby slices, as specified by D. The ROI is a mask covering the region of interest for segmentation. To generate the ROI, a template is built from a set of testing images. The ROI mask can be manually labeled in the template. In the experiments discussed below, the manual segmentation of one testing image is warped to the template through deformable registration. The ROI was then produced by performing a 10 mm dilation to the set of manually labeled voxels in the template space. Given a new testing image, ROI is propagated from the template through deformable registration.

In various exemplary embodiments, the techniques described herein are applied to cardiac anatomy segmentation from axial CT images. To estimate a suitable for such applications, an empirical study may be conducted using axial CT images. One suitable training corpus is the set of images provided for the 2015 MICCAI Multi-Atlas Labeling Challenge. In an exemplary study, the ROI for each image is obtained by performing a 10 mm dilation to the set of non-background voxels in manual segmentation. Label propagation is applied for slices within 30 mm range. Using the data, pairs of intensity difference and label error ($d_F(x)$, $d_L(x)$) are collected at each voxel within ROI in each slice pair that was applied label propagation, from which empirical probability of label error given absolute intensity difference may be calculated as in Equation 5.

$$\hat{p}(v) = \frac{\sum_x I(|d_F(x)| = v, d_L(x) = 1)}{\sum_x I(||d_F(x)|| = v)} \qquad \text{Equation 5}$$

Figure 1:
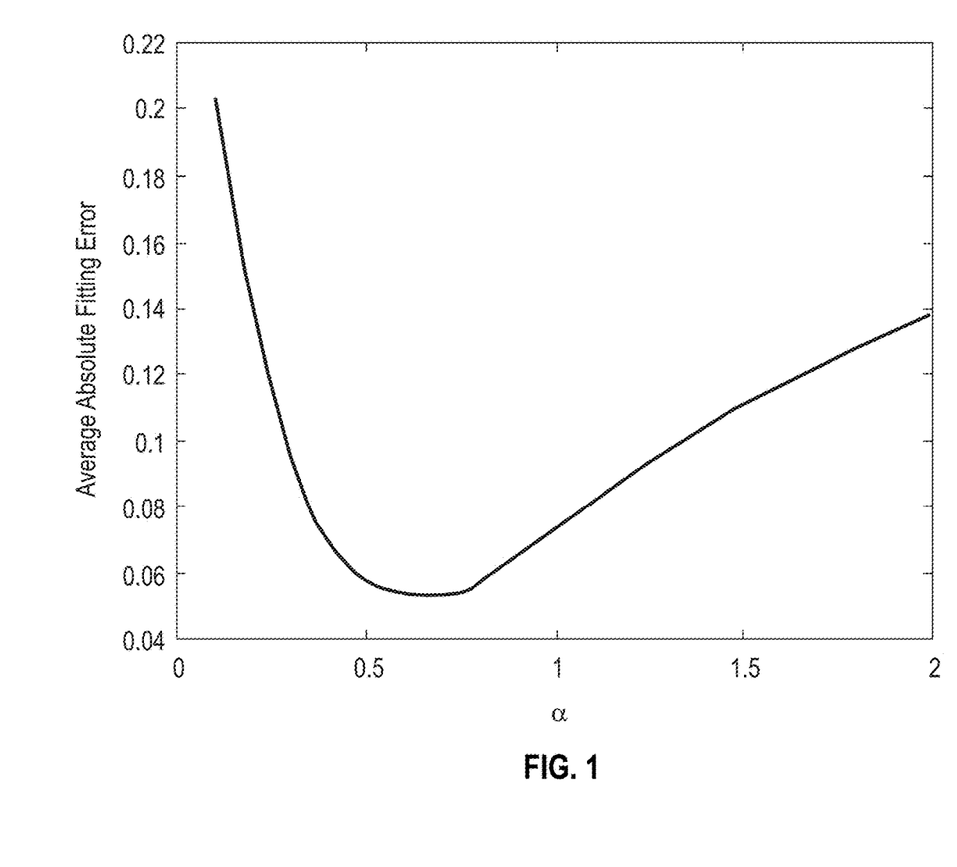
FIG. 1 illustrates average fitting errors according to embodiments of the present disclosure.

A linear model is fitted to minimize the fitting error of Equation 6, where c is a constant. The average fitting errors with respect to a are illustrated in FIG. 1. In this study, α=0.66 produces the least fitting errors for the abdomen CT segmentation data, which may then be applied to compute M in cardiac CT segmentation.

$$e(\alpha) = \sum_x [\hat{p}(|d_F(x)|) - (|d_F(x)|^\alpha + c)]^2 \qquad \text{Equation 6}$$

Figure 2:
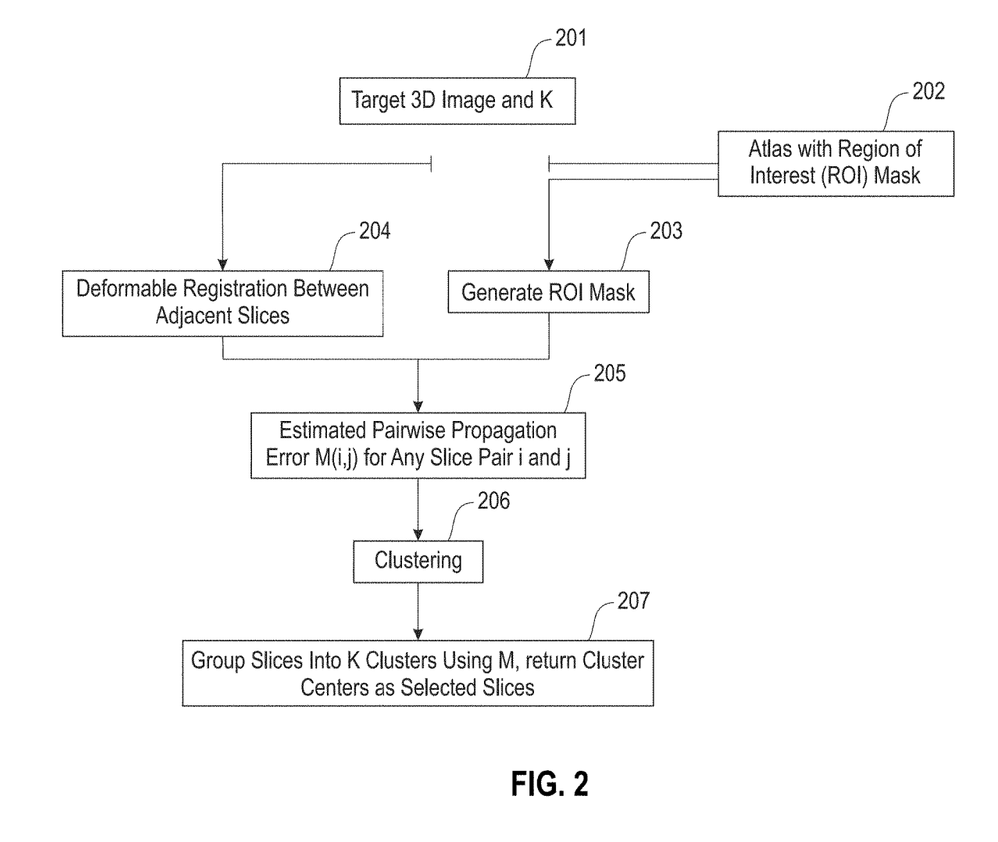
FIG. 2 illustrates an exemplary method of slice selection for interpolation-based 3D manual segmentation is illustrated according to embodiments of the present disclosure.

Referring now to FIG. 2, an exemplary method of slice selection for interpolation-based 3D manual segmentation is illustrated according to embodiments of the present disclosure. At 201, a target 3D image comprising a plurality of slices is read. A target number of slices K is also read. At 202, the image is registered against an atlas to generate a region of interest (ROI) mask at 203. At 204, deformable registration is performed between each adjacent slice. In some embodiments, deformable registration between non-adjacent 2D slices is produced by composing registrations produced for adjacent slices located between the two non-adjacent slices. At 205, estimated pairwise propagation error between any two slices i and j is calculated as set forth above. In some embodiments, estimated pairwise propagation error M(i, j) is defined by Equation 4, as set forth above. In some embodiments, the pairwise propagation error is computed only within the ROI mask, thereby disregarding error stemming from features outside of the region of interest. At 206, k-means clustering is applied to cluster the slices in to K clusters based on the estimated pairwise propagation error M. At 207, the slices corresponding to the center of each of the K clusters are returned as the selected slices. The selected slices may then be supplied to an annotator for annotation.

Accordingly, methods of the present disclosure provide select a subset of 2D slices from a 3D image such that the reconstruction error is minimized using the selected 2D slices to reconstruct 3D segmentation for the image.

Experimental Results

To validate exemplary embodiments of the present disclosure, slice selection methods according to the present disclosure and registration-based interpolation methods according to the concurrently filed commonly owned U.S. application entitled "3D SEGMENTATION RECONSTRUCTION FROM 2D SLICES," which is hereby incorporated by reference, are applied to sample images as set forth below.

Cardiac CT studies were axially acquired by a Siemens CT Scanner (Somatom Definition Flash; Siemens Healthcare, Erlangen, Germany). Each image has isotropic in-plane resolutions, varying from 0.55 $mm^2$ to 0.80 $mm^2$. The slice thickness varies from 0.8 mm to 2.0 mm. A histogram equalization was applied to each image to enhance the intensity contrast between different structures. The histogram equalized images were then resampled to have a 1 $mm^3$ isotropic resolution.

For validation purpose, a set of 16 anatomical structures were manually traced by a clinician using Amira 5.5.0, for 28 cases. The labeled structures include sternum, aorta (ascending/descending/arch/root), pulmonary artery (left/right/trunk), vertebrae, left/right atrium, left/right ventricle, left ventricular myocardium, and superior/inferior vena cava. Intra-rater and inter-rater accuracy was measured in Dice similarity coefficient (DSC) over the 16 structures on 5 randomly selected cases, which is 0.861±0.097 and 0:828±0:071, respectively.

The symmetric normalization (SyN) algorithm was applied as implemented in Advanced Normalization Tools (ANTs) with the cross-correlation similarity metric for deformable registration. Three resolution optimization was applied with maximum 20, 10, and 5 iterations at the coarse, middle and fine levels, respectively.

To obtain a complete profile on how effective slice selection and registration-based interpolation methods are, the slice selection method is applied to select various number of slices from each testing image. The interpolation ratio is defined to be the ratio of total number of slices over the number of selected slices. The interpolation ratio was varied between 3 and 20 for each image. For evaluation, DSC was calculated between each reconstructed 3D segmentation and the respective original manual segmentation.

Registration-based interpolation is compared with shape-based interpolation. To implement shape-based interpolation, a distance map was calculated for each anatomical structure for each selected slice using manual segmentation. The distance maps for an unlabeled slice was produced by linearly interpolating the distance maps from respective propagating slices. The reconstructed segmentation was then derived from voting on its distance maps.

The present slice selection methods are compared with a uniform slice selection scheme. In this uniform selection method, the selected slices are evenly distributed in space among the entire set of slices. If K slices are selected for a 3D volume with n slices, the index of the $k_{th}$ selected slice is $$\left\lfloor \frac{nk}{K+1} + 0.5 \right\rfloor.$$

To investigate the full potential of these slice selection methods, it was also applied using ground truth label propagation errors, where the ground truth inter-slice propagation error was generated by Equation 1 using manual segmentations. The 3D segmentation reconstruction accuracy produced by slices selected from ground truth M provides a upper bound performance for the methods herein.

Figure 3:
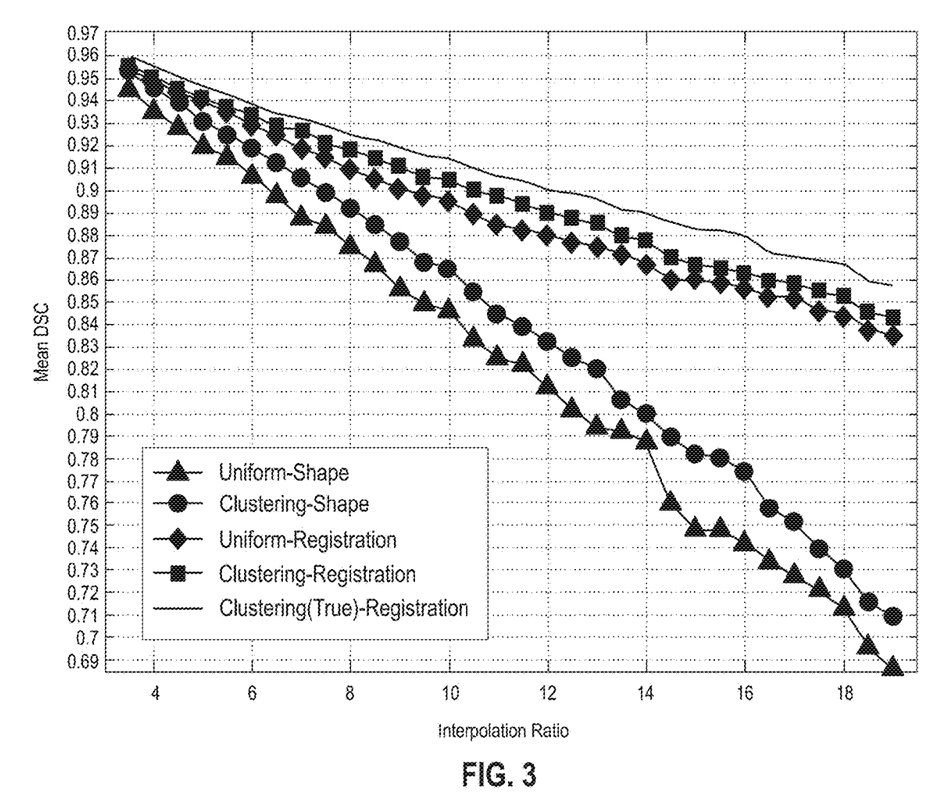
FIG. 3 illustrates observed 3D reconstruction accuracy according to an embodiment of the present disclosure.

FIG. 3 shows the 3D reconstruction accuracy (averaged over all subjects and over all anatomical structures) produced by using different slice selection methods, different interpolation methods and different interpolation ratios. Registration-based interpolation prominently outperformed shape-based interpolation. The advantage of registration-based interpolation is more substantial for long range interpolation tasks, i.e., larger interpolation ratios.

Clustering-based slice selection methods consistently outperformed uniform slice selection. The improvements by registration-based interpolation and by adaptive slice selection are both statistically significant for all interpolation ratios, with p<0:02 on the paired t-test. Although the intensity-based inter-slice propagation error model was empirically fitted on a different dataset, using the model our method approximately reduces the performance gap between uniform selection and the upper bound of our method by half. The performance gap between adaptive slice selection and the upper bound performance increases as interpolation ratio increases. This result indicates that the intensity-based propagation error model is less accurate for slices too far away from each other.

Figure 4A:
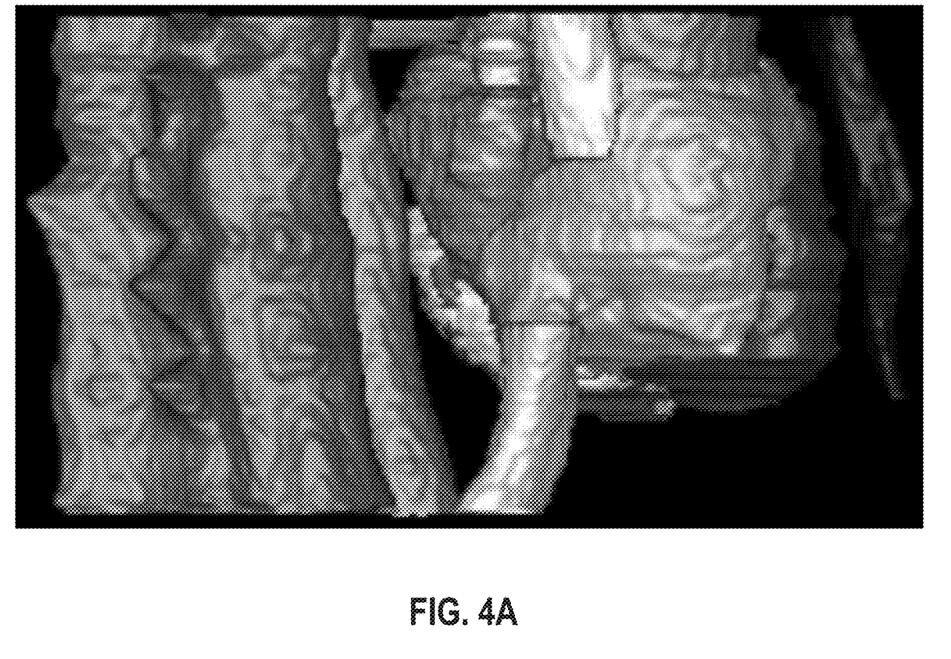
FIGS. 4A-D show exemplary registration-based 3D reconstructions according to various embodiments of the present disclosure.
Figure 4B:
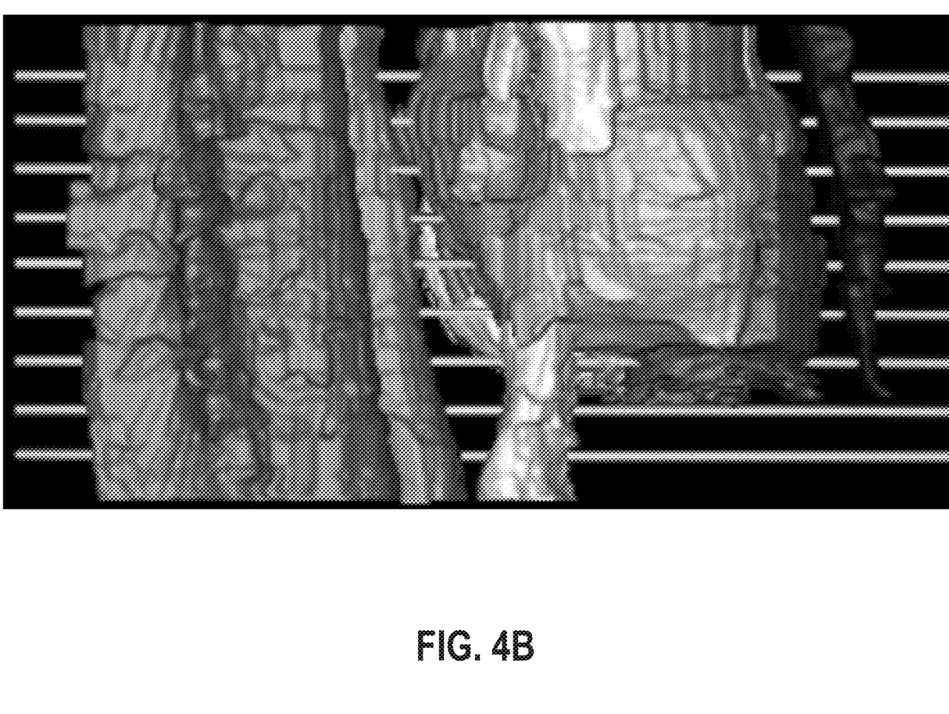
Figure 4C:
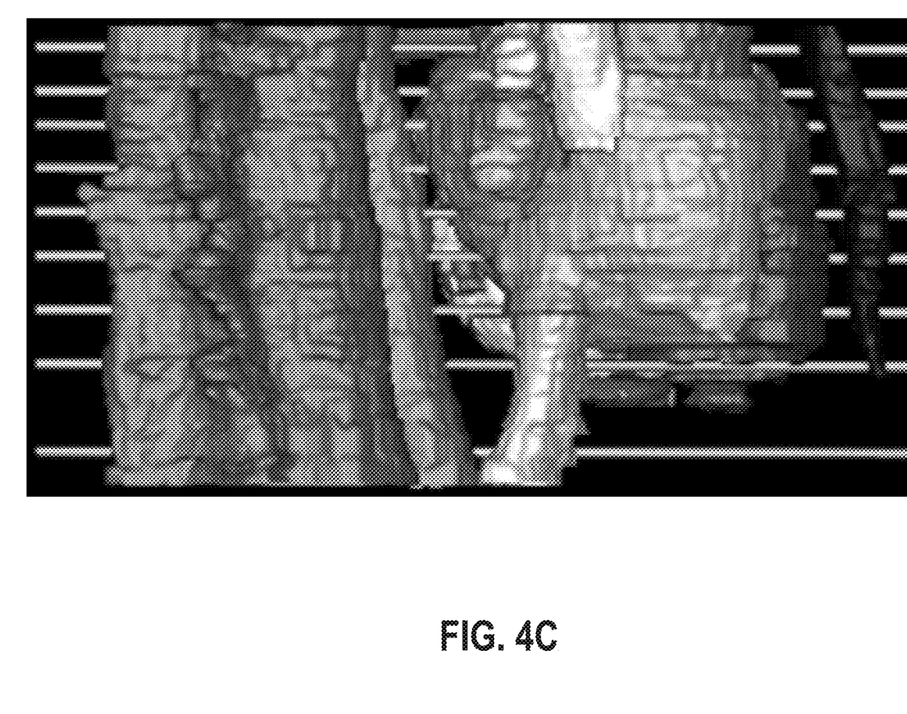
Figure 4D:
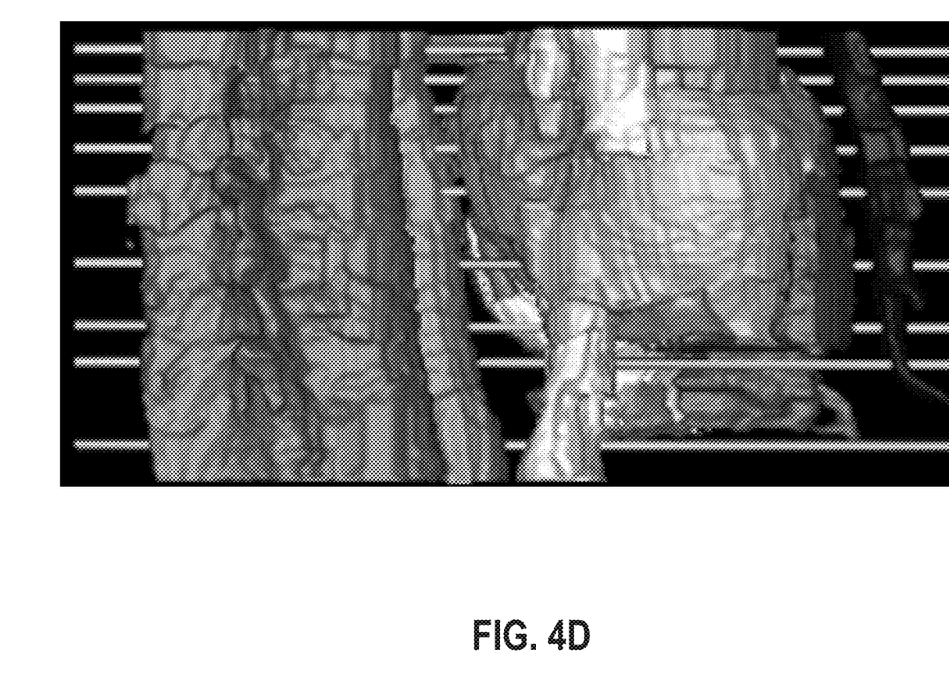

FIGS. 4A-D show examples of registration-based 3D reconstruction from manually segmented axial slices selected by uniform slice selection (FIG. 4B), clustering-based selection (FIG. 4C), and clustering with true inter-slice propagation errors (FIG. 4D). The horizontal lines show the slices selected by each method. The interpolation ratio for this example is 15.

Overall, registration-interpolation saves about 30-40% slices for manual segmentation than shape-based interpolation. Adaptive slice selection further reduces about 10% slices comparing to uniform selection. For example, when shape-based interpolation is applied, average reconstruction accuracy using slices chosen by uniform selection and our slice selection method reaches the intra-rater accuracy level, i.e., 0.86 average DSC, when the interpolation ratios are 9 and 10, respectively. When registration-based interpolation was applied, the interpolation ratios for the two slice selection methods to reach the intra-rater accuracy level are 15 and 16.5, respectively.

Figure 5:
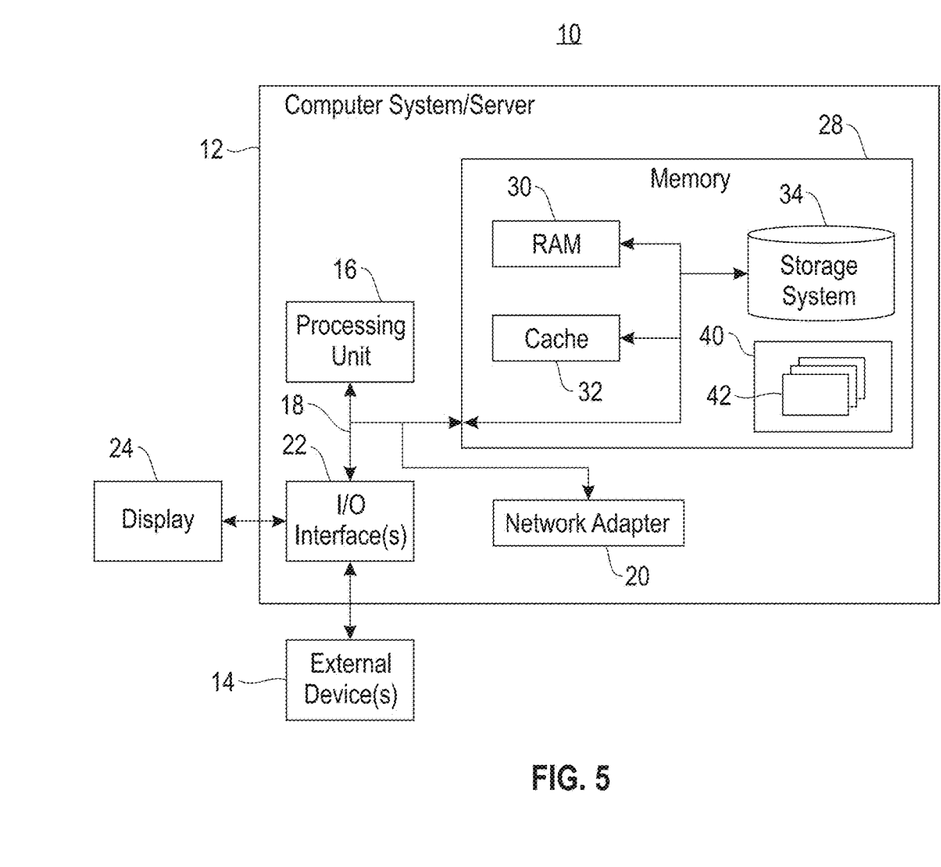
FIG. 5 depicts a computing node according to an embodiment of the present invention.

Referring now to FIG. 5, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   reading a plurality of 2D images, each of the plurality of 2D images representing a slice of a 3D volume;
   performing deformable registration between each adjacent pair of the plurality of 2D images;
   from the deformable registration, estimating propagation error between each pair of the plurality of 2D images;
   clustering the plurality of 2D images into a predetermined number of clusters;
   selecting a slice for annotation from each of the predetermined number of clusters.

2. The method of claim 1, wherein the slice selected from each of the predetermined number of slices is at the center of its cluster.

3. The method of claim 1, wherein clustering the plurality of 2D images comprises applying k-means clustering.

4. The method of claim 1, further comprising:
   determining a region of interest mask for each of the plurality of 2D images, and wherein propagation error is estimated within the region of interest.

5. The method of claim 1, wherein estimating propagation error comprises measuring image intensity differences.

6. The method of claim 1, further comprising:
   providing the selected slices to a user for annotation.

7. The method of claim 1, wherein clustering comprises repeated clustering to determine a minimum overall propagation error.

8. A computer program product for slice selection for interpolation-based 3D manual segmentation, the computer program product comprising a non-transitory computer readable storage medium having program instructions embodied therewith, the program instructions executable by a processor to cause the processor to perform a method comprising:
   reading a plurality of 2D images, each of the plurality of 2D images representing a slice of a 3D volume;
   performing deformable registration between each adjacent pair of the plurality of 2D images;
   from the deformable registration, estimating propagation error between each pair of the plurality of 2D images;
   clustering the plurality of 2D images into a predetermined number of clusters;
   selecting a slice for annotation from each of the predetermined number of clusters.

9. The computer program product of claim 8, wherein the slice selected from each of the predetermined number of slices is at the center of its cluster.

10. The computer program product of claim 8, wherein clustering the plurality of 2D images comprises applying k-means clustering.

11. The computer program product of claim 8, the method further comprising:
    determining a region of interest mask for each of the plurality of 2D images, and wherein propagation error is estimated within the region of interest.

12. The computer program product of claim 8, wherein estimating propagation error comprises measuring image intensity differences.

13. The computer program product of claim 8, the method further comprising:
    providing the selected slices to a user for annotation.

14. The computer program product of claim 8, wherein clustering comprises repeated clustering to determine a minimum overall propagation error.

15. A system comprising:
    a first datastore comprising a plurality of 2D images, each of the plurality of 2D images representing a slice of a 3D volume;
    a computing node comprising a computer readable storage medium having program instructions embodied therewith, the program instructions executable by a processor of the computing node to cause the processor to perform a method comprising:

reading the plurality of 2D images from the first datastore;

performing deformable registration between each adjacent pair of the plurality of 2D images;

from the deformable registration, estimating propagation error between each pair of the plurality of 2D images;

clustering the plurality of 2D images into a predetermined number of clusters;

selecting a slice for annotation from each of the predetermined number of clusters.

16. The system of claim 15, wherein the slice selected from each of the predetermined number of slices is at the center of its cluster.

17. The system of claim 15, wherein clustering the plurality of 2D images comprises applying k-means clustering.

18. The system of claim 15, the method further comprising:

determining a region of interest mask for each of the plurality of 2D images, and wherein propagation error is estimated within the region of interest.

19. The system of claim 15, wherein estimating propagation error comprises measuring image intensity differences.

20. The system of claim 15, the method further comprising:

providing the selected slices to a user for annotation.

* * * * *